US012715295B2

(12) United States Patent
Sim et al.

(10) Patent No.: US 12,715,295 B2
(45) Date of Patent: Aug. 25, 2026

(54) APPARATUS AND METHOD FOR CONTROLLING A VEHICLE AND POWERING MEDICAL EQUIPMENT IN THE VEHICLE

(71) Applicants: Hyundai Motor Company, Seoul (KR); Kia Corporation, Seoul (KR)

(72) Inventors: Ki Seon Sim, Suwon-si (KR); Hee Chang Oh, Seongnam-si (KR); Jae Heun Kim, Hwaseong-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 74 days.

(21) Appl. No.: 18/764,675

(22) Filed: Jul. 5, 2024

(65) Prior Publication Data

US 2025/0100387 A1 Mar. 27, 2025

(30) Foreign Application Priority Data

Sep. 21, 2023 (KR) ........................ 10-2023-0126457

(51) Int. Cl.
*B60L 53/60* (2019.01)
*A61B 5/117* (2016.01)
(Continued)

(52) U.S. Cl.
CPC .............. *B60L 1/003* (2013.01); *A61B 5/117* (2013.01); *B60L 53/60* (2019.02); *H02J 7/855* (2026.01);
(Continued)

(58) Field of Classification Search
CPC . B60L 1/003; B60L 53/60; B60L 1/00; A61B 5/117; A61B 5/0015; A61B 5/0077; A61B 5/14542; A61B 2505/01; A61B 5/0205; A61B 5/021; A61B 5/6893; A61B 5/0002; H02J 7/0063; B60N 2/0226; B60N 2/20; B60N 2/14; B60R 16/033; A61G 3/001; A61G 2203/10; A61G 2203/20; A61G 2203/70; H04W 4/40; B60Y 2200/91
See application file for complete search history.

(56) References Cited

U.S. PATENT DOCUMENTS

2023/0381038 A1* 11/2023 Koga .................... G16H 30/20

FOREIGN PATENT DOCUMENTS

JP 2021078278 A * 5/2021

* cited by examiner

*Primary Examiner* — Michael C Zarroli
(74) *Attorney, Agent, or Firm* — Slater Matsil, LLP

(57) ABSTRACT

A vehicle control device for a host vehicle can include a processor, a power supply device that performs charging or discharging, a first battery used to operate the host vehicle, and memory. The processor may charge the first battery based on a charge power supplied from an external power source through the power supply device, perform control of the host vehicle such that the vehicle drives to a place other than a medical facility for use of medical equipment, provide power to the medical equipment based on a discharge power supplied by the first battery through the power supply device, and control the medical equipment such that the medical equipment performs one of or both of identifying a condition of a patient at the place and performing treatment on the patient at the place using the medical equipment, wherein the power is supplied to enable use of the medical equipment.

20 Claims, 8 Drawing Sheets

(51) Int. Cl.
*B60L 1/00* (2006.01)
*B60N 2/02* (2006.01)
*B60N 2/20* (2006.01)
*B60R 16/033* (2006.01)
*H02J 7/00* (2026.01)

(52) U.S. Cl.
CPC .............. *B60N 2/0226* (2023.08); *B60N 2/20* (2013.01); *B60R 16/033* (2013.01)

APPARATUS AND METHOD FOR CONTROLLING A VEHICLE AND POWERING MEDICAL EQUIPMENT IN THE VEHICLE

CROSS-REFERENCE TO RELATED APPLICATIONS

This application claims the benefit of Korean Patent Application No. 10-2023-0126457, filed on Sep. 21, 2023, which application is hereby incorporated herein by reference.

TECHNICAL FIELD

The present disclosure relates to a vehicle control device and method for supplying power to an electronic device by an electric vehicle.

BACKGROUND

Recently, as climate change and environmental pollution problems intensify, global efforts to reduce carbon emissions are being urged. In line with these demands, commercialization of technology for hybrid vehicles or electric vehicles with low carbon emissions and fossil fuel consumption is underway.

A hybrid vehicle or an electric vehicle refers to a vehicle that charges electrical energy from an external power source through a battery included in the vehicle and uses the charged electrical energy for driving. The hybrid vehicle or the electric vehicle may charge or operate an electronic device through electrical energy stored in the battery. The hybrid vehicle or the electric vehicle may improve user convenience through this two-way power conversion. In addition, as some or all of the power generation devices of existing internal combustion engine vehicles, such as engines, are removed or converted, the power generation devices are miniaturized, allowing the hybrid vehicle or the electric vehicle to secure a large loading space.

SUMMARY

The present disclosure relates to a vehicle control device and method, and more particularly, to a technology for supplying power to an electronic device through an electric vehicle.

Some embodiments of the present disclosure can solve the above-mentioned problems occurring in the prior art while advantages achieved by the prior art are maintained intact.

An embodiment of the present disclosure can provide a vehicle control device and method capable of operating medical equipment by providing power from a hybrid vehicle or an electric vehicle.

In some embodiments of the present disclosure, a vehicle control device and method can be capable of improving user convenience by operating medical equipment through power provided by a hybrid vehicle or an electric vehicle.

In some embodiments of the present disclosure, a vehicle control device and method can be capable of expanding the scope of medical services available to patients by operating medical equipment using power provided by a hybrid vehicle or an electric vehicle.

In some embodiments of the present disclosure, a vehicle control device and method can be capable of providing medical services to patients who are far from the medical staff by operating medical equipment using power provided by a hybrid vehicle or an electric vehicle.

In some embodiments of the present disclosure, a vehicle control device and method can be capable of accessing patient medical records even outside hospitals by operating medical equipment using power provided by a hybrid vehicle or an electric vehicle.

Technical problems solved by some embodiments of the present disclosure are not necessarily limited to the aforementioned problems, and solutions to other technical problems can be clearly understood from the following description by those skilled in the art to which the present disclosure pertains.

According to an embodiment of the present disclosure, a vehicle control device includes a power supply device included in a host vehicle, that performs charging or discharging, wherein the host vehicle is an electric vehicle (EV), a first battery configured to be used to operate the host vehicle, a processor, and memory storing instructions that, when executed by the processor.

According to an embodiment of the present disclosure, the processor may charge the first battery based on a charge power supplied from an external power source through the power supply device, perform control of the host vehicle such that the host vehicle drives to a place other than a medical facility for use of medical equipment, provide power to the medical equipment based on a discharge power supplied by the first battery through the power supply device, and perform one of or both of identifying a condition of a patient through the medical equipment at the place and performing treatment on the patient.

According to an embodiment of the present disclosure, a vehicle control device may further include a communication circuit. The processor may transmit patient condition information obtained through the medical equipment to an external server or a hospital through the communication circuit, receive an opinion of a medical staff according to the patient condition information through the communication circuit, and output the opinion of the medical staff through an output device provided in the host vehicle or the medical equipment.

According to an embodiment of the present disclosure, a vehicle control device may further include a camera and a monitor. The processor may obtain the patient condition information through at least one of the camera or the medical equipment, and output the opinion of the medical staff through the monitor.

According to an embodiment of the present disclosure, a vehicle control device may further include a communication circuit. The processor may transmit identification information for identifying the patient to an external server or a hospital through the communication circuit, receive a medical record of the patient identified based on the identification information from the external server or the hospital through the communication circuit, and output the medical record through an output device provided in the host vehicle or the medical equipment.

According to an embodiment of the present disclosure, the processor may transmit the patient condition information through wireless communication using a communication protocol for transmitting or receiving medical information, and receive the opinion of the medical staff through the wireless communication using the communication protocol.

According to an embodiment of the present disclosure, the processor may provide a rated voltage of the medical equipment to the medical equipment through the power supply device and wherein the power supply device includes an integrated charging control unit (ICCU).

According to an embodiment of the present disclosure, the medical equipment may include at least one of an oxygen supply device, a defibrillator, a dialysis machine, a vital monitor, an aspirator, a laryngoscope, or any combination thereof.

According to an embodiment of the present disclosure, the processor may provide an interface for operating a vehicle seat such that a seat angle between a lower end of the vehicle seat and a backrest of the vehicle seat is adjusted to a first angle or greater than the first angle. According to an embodiment of the present disclosure, the processor may provide an interface for operating a turning seat such that the turning seat is adjusted to face a second seat by rotating the turning seat.

According to an embodiment of the present disclosure, a vehicle control device may further include a spare battery that is different from the first battery. The processor may continuously supply power to the medical equipment through the spare battery in response to the first battery being discharged after powering the medical equipment with the first battery.

According to an embodiment of the present disclosure, the processor may obtain the place, and a specified frequency, included in a subscription service, perform control such that the host vehicle drives to the place regularly according to the specified frequency or irregularly upon request, and perform one of or both of identifying the condition of the patient at the place and performing treatment on the patient through the medical equipment at the place.

According to an embodiment of the present disclosure, the medical equipment includes a dialysis machine. The processor may supply power to the dialysis machine from the first battery through the power supply device. The dialysis machine may provide hemodialysis to the patient.

According to an embodiment of the present disclosure, a vehicle control method includes charging a first battery of a host vehicle based on a charge power supplied from an external power source through a power supply device of the host vehicle, performing control such that the host vehicle drives to a place other than a medical facility to user medical equipment, providing power to the medical equipment based on a discharge power supplied by the first battery through the power supply device, and identifying a condition of a patient or performing treatment on the patient through the medical equipment at the place.

According to an embodiment of the present disclosure, a vehicle control method may further include transmitting patient condition information obtained through the medical equipment to an external server or a hospital, receiving an opinion of a medical staff according to the patient condition information, and outputting the opinion of the medical staff through an output device provided in the host vehicle or the medical equipment.

According to an embodiment of the present disclosure, identifying the condition of the patient comprises obtaining the patient condition information through at least one of a camera or the medical equipment, and wherein the outputting of the opinion of the medical staff through the output device comprises outputting the opinion of the medical staff through a monitor.

According to an embodiment of the present disclosure, a vehicle control method may further include transmitting identification information to identify the patient to an external server or a hospital, receiving a medical record of the patient identified based on the identification information from the external server or the hospital, and outputting the medical record through an output device provided in the host vehicle or the medical equipment.

According to an embodiment of the present disclosure, transmitting the patient condition information includes transmitting the patient condition information through wireless communication using a communication protocol for transmitting or receiving medical information. The receiving of the opinion of the medical staff may include receiving the opinion of the medical staff through the wireless communication using the communication protocol.

According to an embodiment of the present disclosure, the providing of the power to the medical equipment may include providing a rated voltage of the medical equipment to the medical equipment through the power supply device that includes an integrated charging control unit (ICCU).

According to an embodiment of the present disclosure, the medical equipment may include at least one of an oxygen supply device, a defibrillator, a dialysis machine, a vital monitor, an aspirator, a laryngoscope.

According to an embodiment of the present disclosure, the vehicle control method may further include providing an interface for operating a vehicle seat such that a seat angle between a lower end of the vehicle seat and a backrest of the vehicle seat is adjusted to a first angle or more.

BRIEF DESCRIPTION OF THE DRAWINGS

The above and other features and advantages of the present disclosure can be more apparent from the following detailed description taken in conjunction with the accompanying drawings, in which.

DETAILED DESCRIPTION OF ILLUSTRATIVE EMBODIMENTS

Figure 1:
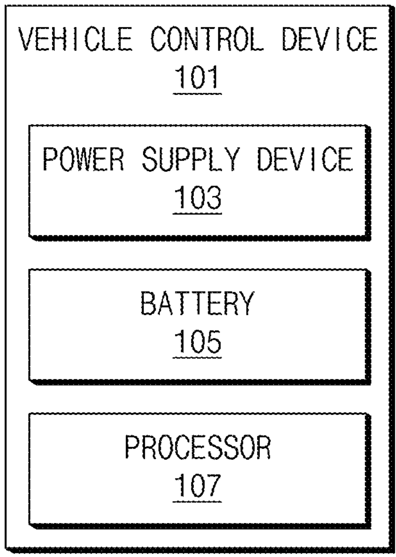
FIG. 1 is a block diagram showing the configuration of a vehicle control device according to an embodiment of the present disclosure.

Hereinafter, some embodiments of the present disclosure will be described in detail with reference to the example drawings. In adding the reference numerals to the components of each drawing, identical or equivalent components can be designated by identical numerals even when they are displayed on other drawings. Further, in describing embodiments of the present disclosure, a detailed description of well-known features or functions can be omitted to not unnecessarily obscure the gist of the present disclosure.

In describing the components of an embodiment according to the present disclosure, terms such as “first”, “second”, “A”, “B”, “(a)”, “(b)”, and the like, may be used. Such terms can be merely intended to distinguish one component from another component, and such terms do not necessarily limit the nature, sequence, or order of the constituent components. Unless otherwise defined, terms used herein, including technical or scientific terms, can have a same meaning as those generally understood by those skilled in the art to which the present disclosure pertains. Such terms as those defined in a generally used dictionary can be interpreted as having meanings based on the contextual meanings in the relevant field of art.

Hereinafter, embodiments of the present disclosure will be described in detail with reference to FIGS. 1 to 8.

FIG. 1 is a block diagram showing the configuration of a vehicle control device according to an embodiment of the present disclosure.

A vehicle control device 101 according to an embodiment of the present disclosure may be implemented inside or outside a vehicle, and some or all of components included in the vehicle control device 101 may be implemented inside or outside the vehicle.

Referring to FIG. 1, the vehicle control device 101 may include at least one of a power supply device 103, a battery 105, a processor 107, or any combination thereof. At least one of the power supply device 103, the battery 105, the processor 107, or any combination thereof may be electronically and/or operably coupled with each other by an electronic component, such as a communication bus.

According to some embodiments, hereinafter, combining pieces of hardware operatively can refer to a direct connection or an indirect connection between the pieces of hardware being established in a wired or wireless manner such that first hardware of the pieces of hardware can be controlled by second hardware of the pieces of hardware. The type and/or number of hardware included in the vehicle control device 101 is not necessarily limited to that shown in FIG. 1. In some embodiments, the vehicle control device 101 may include only some of hardware components shown in FIG. 1.

According to an embodiment, the power supply device 103 may charge the battery 105 based on a charge power supplied from an external power source. The power supply device 103 may provide power to an external electronic device based on a discharge power supplied by the battery. In other words, a host vehicle that is an electric vehicle (EV) can be capable of two-way power conversion through the power supply device 103.

According to an embodiment, the battery 105 may store electrical energy for operating the host vehicle. In other words, the battery 105 may be charged based on a charge power supplied from an external power source. As the battery 105 is discharged, the battery 105 may provide a discharge power to an external electronic device or provide the discharged power for the operation of the host vehicle.

According to an embodiment, the processor 107 of the vehicle control device 101 may charge the battery 105 through the power supply device 103 or provide a power to an external electronic device by discharging the battery 105. For example, external electronic devices may include medical equipment (e.g., oxygen delivery devices, defibrillators, dialysis machines, vital monitors, aspirators, laryngoscopes, in singular or plural, or any combinations thereof).

According to an embodiment, the processor 107 of the vehicle control device 101 may perform control such that the vehicle drives to a specific location. For example, the specific location may include locations other than medical facilities and where there is a need to use medical equipment.

According to an embodiment, the processor 107 of the vehicle control device 101 may determine a patient’s condition through medical equipment and/or perform treatment on the patient at the specific location. For example, a dialysis machine powered from battery 105 via the power supply device 103 may provide hemodialysis to a patient.

When the main battery is discharged while supplying power to the medical equipment, the processor 107 of the vehicle control device 101 may continuously supply power to the medical equipment through a spare battery which is different from the main battery. By preparing for emergency situations through a spare battery, the vehicle control device 101 may ensure stability.

According to an embodiment, the processor 107 of the vehicle control device 101 may perform control such that the host vehicle drives to a place other than a medical facility and where there is a need to use medical equipment, and then determine a patient’s condition and/or perform treatment on the patient through the medical equipment based on the power supplied through the battery 105.

According to an embodiment, the processor 107 of the vehicle control device 101 may not only determine the patient’s condition through medical equipment and/or perform treatment on the patient, but also transmit the patient’s condition to a distant medical staff and output the opinions of medical staff (e.g., doctors, nurses, paramedics, oriental medicine doctors, midwives, dentists).

In other words, the processor 107 of the vehicle control device 101 may transmit condition information obtained through a camera (or cameras) or medical equipment that is indicating the patient’s condition to an external server or hospital through a communication circuit. The processor 107 of the vehicle control device 101 may receive the medical staff’s opinions according to the patient’s condition information through the communication circuit. The processor of the vehicle control device 101 may output the opinions of the medical staff through an output device installed in the host vehicle or the medical equipment (e.g., a vehicle monitor, a vehicle speaker, a printer, a fax, a refreshable braille display, a monitor or speaker included in the medical equipment, singular or plural thereof, or any combination thereof).

According to an embodiment, the processor 107 of the vehicle control device 101 may identify the patient’s medical records at a location other than a medical facility. For example, the processor 107 of the vehicle control device 101 may transmit identification information (e.g., name, resident registration number, medical number) necessary or useful to identify a patient to an external server or a hospital through the communication circuit. The processor 107 of the vehicle control device 101 may receive the medical records of the patient identified based on the identification information from the external server or the hospital through the communication circuit. The medical records may include the patient’s medical record. The medical records may include administrative information, sign and symptom information, diagnostic information, medical history information, or any combination thereof, regarding the patient. The processor 107 of the vehicle control device 101 may output the medical records through an output device provided in the host vehicle or medical equipment.

According to an embodiment, the vehicle control device 101 may expand medical accessibility for patients living in areas with few medical facilities or for patients with limited mobility. Details related to the expansion of medical accessibility will be described below with reference to FIG. 6.

A host vehicle including the vehicle control device 101 may include a specific type of seat to provide medical services. Types of seats will be described below with reference to FIG. 2.

The host vehicle including the vehicle control device 101 may include medical equipment arranged at a specific location to provide medical services. The arrangement of the medical equipment will be described below with reference to FIG. 3.

Figure 2:
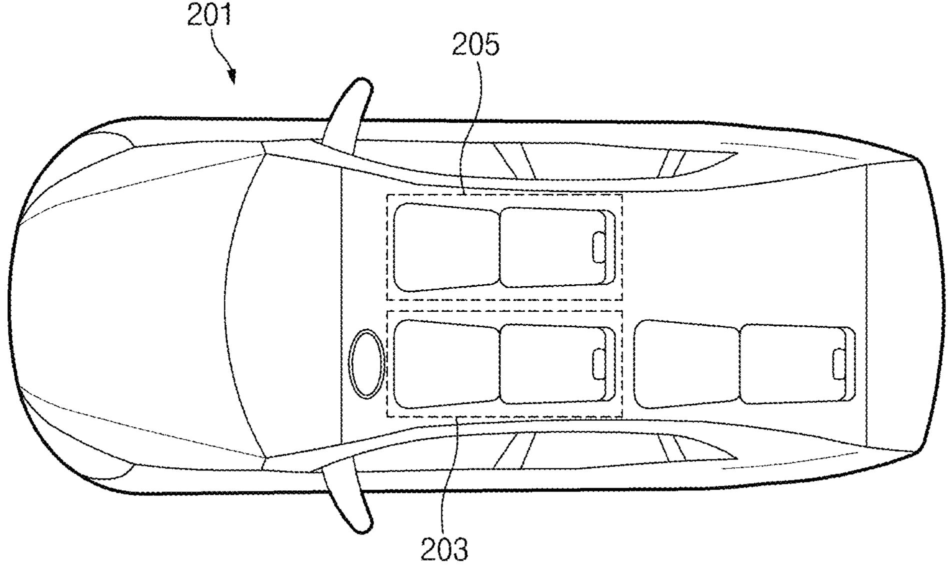
FIG. 2 is a diagram showing example seat arrangements in a vehicle control device or a vehicle control method according to an embodiment of the present disclosure.
Figure 2:
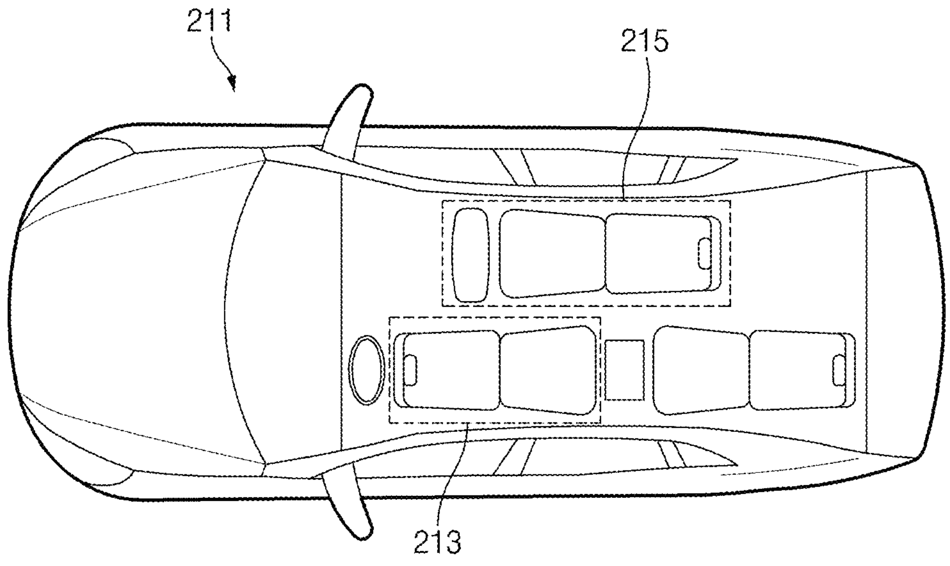

FIG. 2 shows two cars 201 and 211, and examples of seat arrangements in a vehicle control device or a vehicle control method according to an embodiment of the present disclosure.

Referring to FIG. 2, in a first car 201, such as a hybrid vehicle or an electric vehicle, is in a first state, which may be in a driving state. In a second car 211 in a second state, medical equipment may operate according to power supplied by the hybrid vehicle or the electric vehicle. As the medical equipment operates, condition information indicating the patient's condition may be obtained, the patient may receive medical treatment, a medical consultation may be performed with a remotely located medical staff, the patient's medical records may be obtained, or any combination thereof.

A first seat (e.g., a first seat 203 in the first car 201, or a first seat 213 in the second car 211) may be a turning seat that can be adjusted by rotating the seat such that the seat faces a different seat. A second seat (e.g., a second seat 205 in the first car 201, or a second seat 215 in the second car 211) may be a seat capable of laying fully flat or a seat of which a seat angle formed between the bottom of the seat and the backrest of the seat can be adjusted to a specified angle or more.

According to an embodiment, in the first car 201 in the first state, the first seat 203 and the second seat 205 may be arranged to face the front of the host vehicle. Arranging a seat (e.g., the first seat 203 in the first car 201, or the second seat 205 in the first car 201) to face the front of the host vehicle may correspond to the two areas separated by the surface corresponding to the backrest of the seat, that is, an area containing the lower end of the seat and an area containing the front of the host vehicle can be similarly angle/positions or identical to each other.

The processor of the vehicle control device may provide an interface for operating a turning seat in which, the first seat 203 in the first state can be adjusted by rotating the first seat 203 such that the first seat 203 faces a seat different from the first seat 203. The processor of the vehicle control device may rotate the first seat 203 based on a user input obtained through the interface.

According to an embodiment, in the second car 211 in a second state, the first seat 213 may be arranged to face the rear of the host vehicle. Arranging a seat (e.g., the first seat 213 in the second car 211) to face the rear of the host vehicle may correspond to the two areas separated by the surface corresponding to the backrest of the seat, that is, an area containing the lower end of the seat and an area containing the front of the host vehicle can be different from each other.

Rotating the first seat 203 in the first state like the first seat 213 in the second state can secure a wider space and improve the convenience of a patient and a guide in the host vehicle. According to an embodiment, the guide may include a medical staff. The medical staff may check the patient's condition and perform necessary treatment using medical equipment. According to an embodiment, the guide may play the role of collecting the patient's condition to transfer the patient's condition to a medical staff.

In the first state shown in the first car 201, the angle formed between the lower end of the second seat 205 and the backrest of the second seat 205 (e.g., about 90°) may be greater than or equal to a specified angle. The processor of the vehicle control device may provide an interface for operating a seat in which, in the first state shown in the first car 201, the angle formed between the lower end of the second seat 205 and the backrest of the second seat 205 can be adjusted to a specified angle or more (e.g., flattening the seat for a laying position). The processor of the vehicle control device may adjust the angle of the backrest of the second seat 205 based on a user input obtained through the interface.

In the second state shown in the second car 211, the angle formed between the lower end of the second seat 215 and the backrest of the second seat 215 (e.g., approximately 0°) may be greater than or equal to a specified angle. For example, the second seat 215 in the second state shown in the second car 211 may be in a full flat state.

The second seat 215 may be a full flatten seat to allow a patient to receive medical treatment in a comfortable position or in a laying position. However, embodiments of the present disclosure may not be limited thereto. The second seat may not be a full flat seat, but may be a seat that reclines beyond a specified angle, for example.

Figure 3:
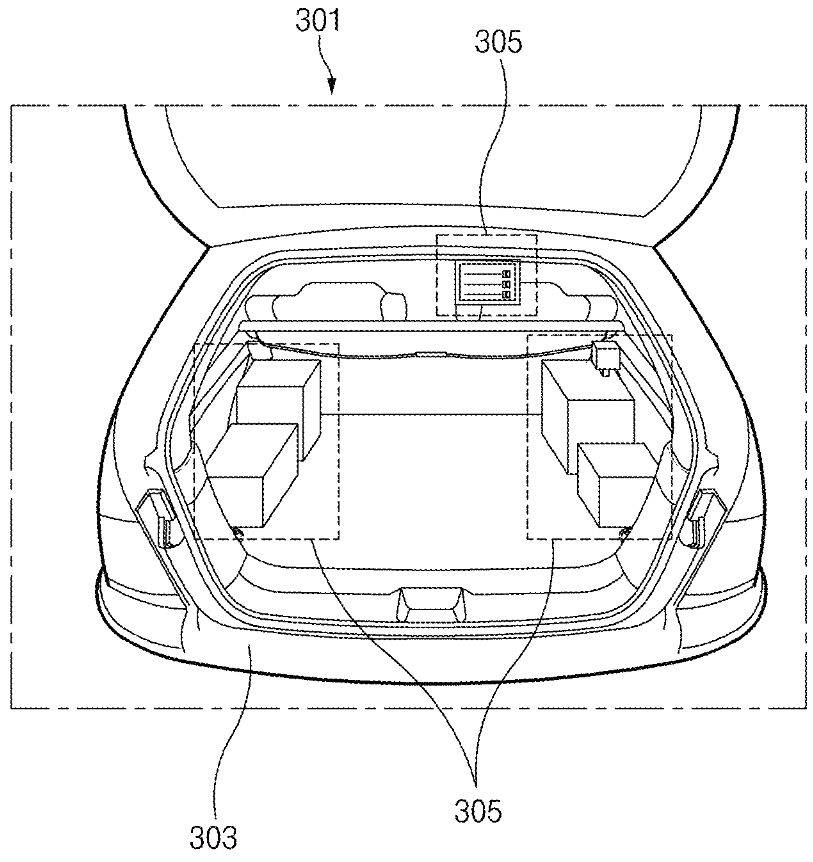
FIG. 3 is diagram showing an example arrangement of medical equipment in a vehicle control device or a vehicle control method according to an embodiment of the present disclosure.

FIG. 3 shows an example arrangement of medical equipment in a vehicle control device or a vehicle control method according to an embodiment of the present disclosure.

Referring to FIG. 3, in a situation 301, a host vehicle 303, which can be an electric vehicle, may supply power to medical equipment 305 through a battery.

According to an embodiment, the medical equipment 305 may include an oxygen supply device, a dialysis machine, a vital monitor, a monitor, emergency medical equipment, in singular or plural thereof, or any combination thereof, for example. However, embodiments of the present disclosure may not be limited thereto. The emergency medical equipment may include defibrillators, suction machines, and laryngoscopes, for example.

Because the electric vehicle does not require equipment such as an engine, transmission, or fuel tank, the loading space of the electric vehicle according to an embodiment may be wider than that of a conventional internal combustion engine vehicle. A host vehicle equipped with the vehicle control device may load medical equipment into its spacious loading space. The living space and loading space of the host vehicle including the vehicle control device may be designed in various ways. According to an embodiment, the medical equipment may be loaded into the trunk. However, embodiments of the present disclosure may not be limited thereto.

According to an embodiment, when a patient with renal failure uses the host vehicle equipped with the vehicle control device, the patient may receive hemodialysis in a full-flat seat through a dialysis machine loaded in the trunk, for example. The patient may receive hemodialysis in a comfortable environment with indoor air conditioning and heating. The medical staff may monitor the dialysis machine or vital equipment through a monitor attached to the ceiling of the host vehicle.

Figure 4:
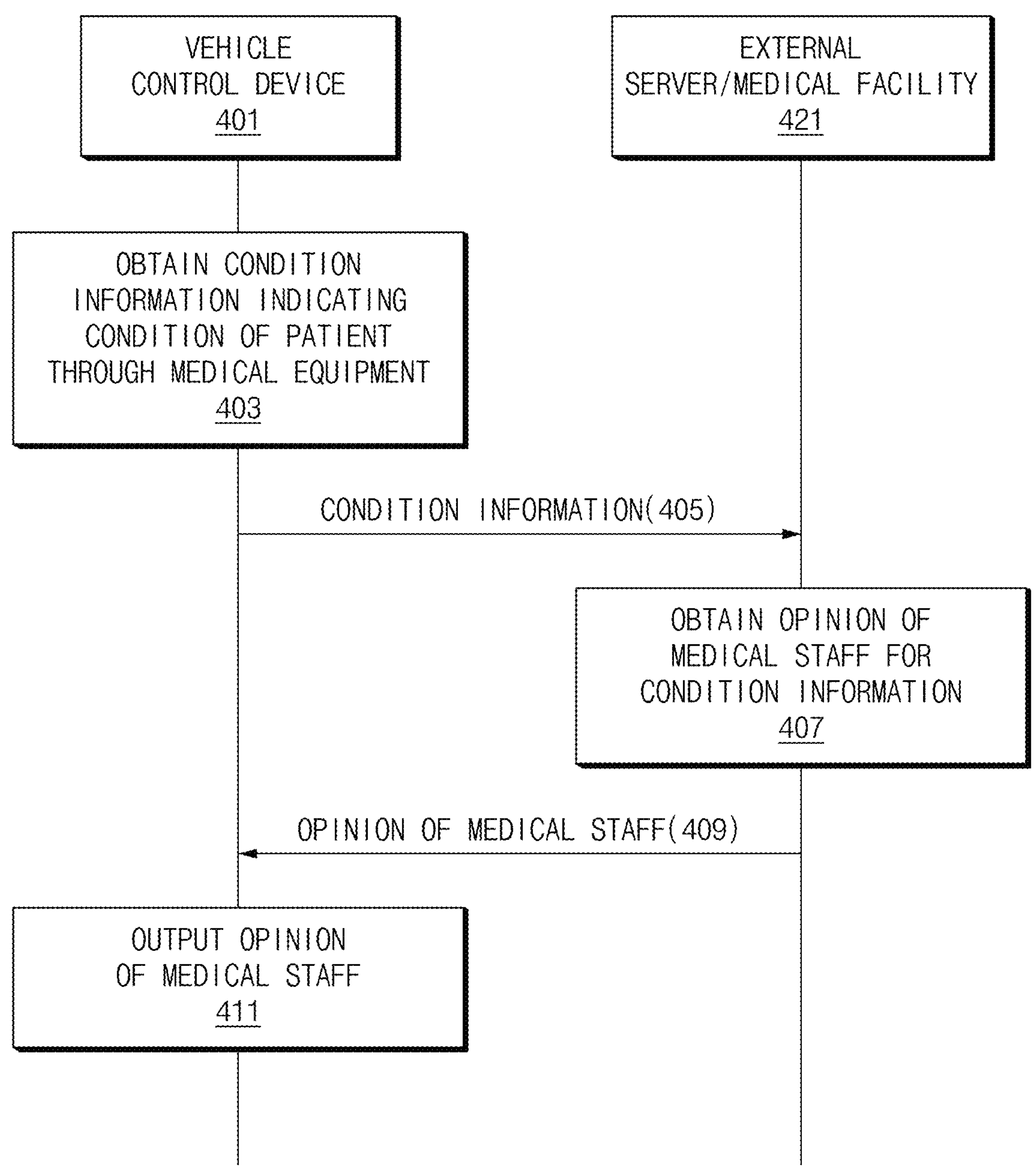
FIG. 4 is a flowchart showing an example of signaling between a vehicle control device and an external server to obtain a medical staff's opinion in a vehicle control device or a vehicle control method according to an embodiment of the present disclosure.

FIG. 4 shows an example of signaling between a vehicle control device and an external server to obtain a medical staff's opinion in a vehicle control device or a vehicle control method according to an embodiment of the present disclosure.

Hereinafter, it is assumed that the vehicle control device 101 of FIG. 1 performs the process of FIG. 4, as an example embodiment thereof. Additionally, in the description of FIG. 4, operations described as being performed by the vehicle control device may be understood as being controlled by the processor 107 of the vehicle control device 101.

Referring to FIG. 4, in a first operation 403, a vehicle control device 401 may obtain condition information indicating the patient's condition through medical equipment. For example, the condition information may include at least one of the patient's pulse information, blood pressure information, body temperature information, oxygen saturation information, appearance information, organ condition information through X-rays, or any combination thereof, for example.

In a second operation 405, the vehicle control device 401 may transmit the condition information to an external server or medical facility 421. The external server or medical facility 421 may receive the condition information from the vehicle control device 401.

The vehicle control device 401 may transmit the condition information through wireless communication using a communication protocol for transmitting or receiving medical information (e.g., health level seven (HL7), fast healthcare interoperability resources (FHIR)). This can be to prevent medical information from being leaked.

In a third operation 407, the external server or medical facility 421 may obtain the medical staff's opinion of the condition information. A medical staff located in a location different from where the host vehicle is located may submit opinions on the received patient's condition information.

In a fourth operation 409, the external server or medical facility 421 may transmit the medical staff's opinions to the vehicle control device 401. The vehicle control device 401 may receive the medical staff's opinions from the external server or medical facility 421.

The vehicle control device 401 may receive the medical staff's opinions through wireless communication using a communication protocol for transmitting or receiving medical information (e.g., health level seven (HL7) or fast healthcare interoperability resources (FHIR)). This can be to prevent medical information from being leaked.

In a fifth operation 411, the vehicle control device 401 may output the medical staff's opinions. For example, the vehicle control device 401 may output the opinions of the medical staff through an output device installed in the host vehicle or the medical equipment (e.g., a vehicle monitor, a vehicle speaker, a printer, a fax, a refreshable braille display, a monitor or speaker included in the medical equipment).

Figure 5:
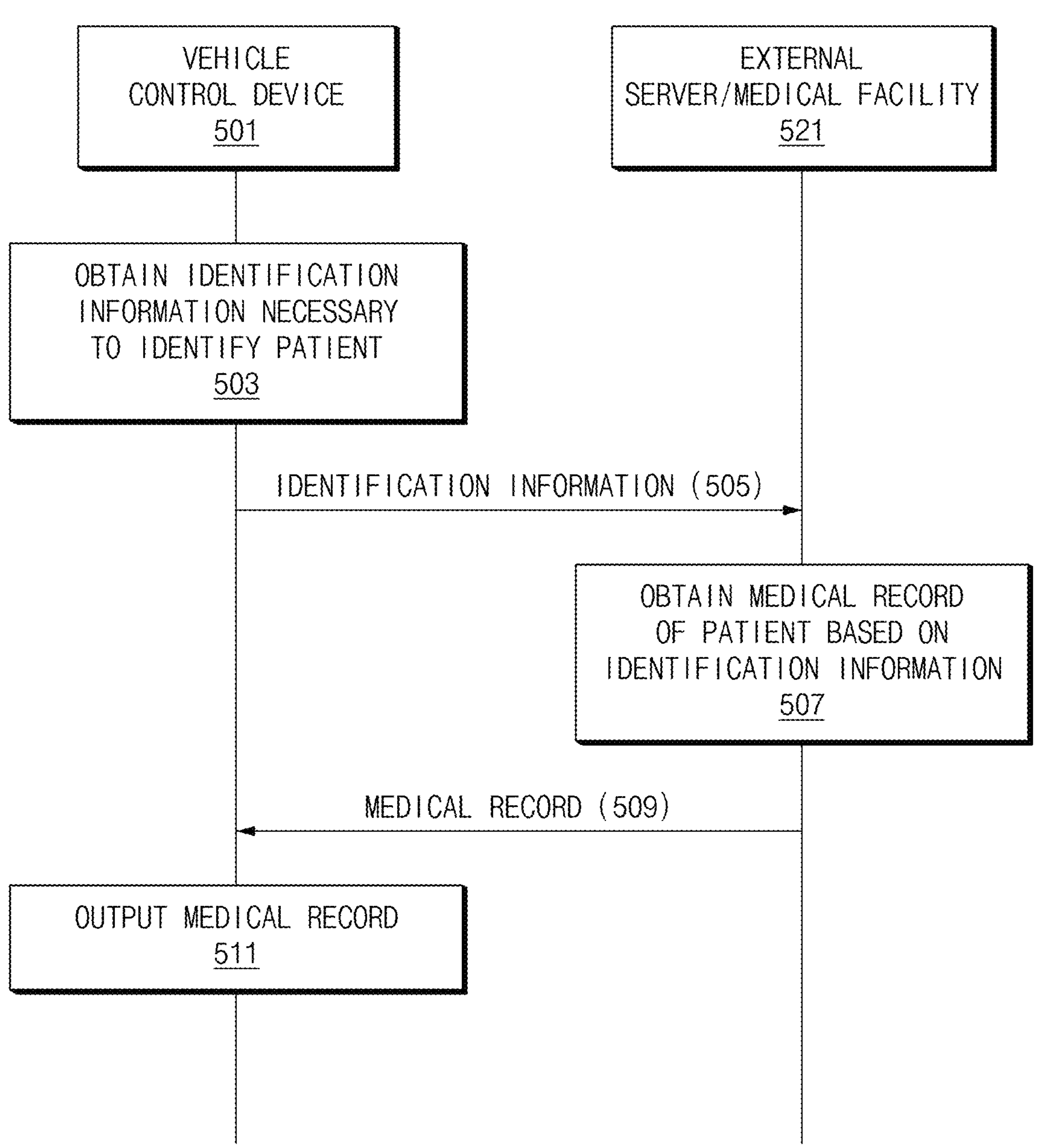
FIG. 5 is a flowchart showing an example of signaling between a vehicle control device and an external server to obtain medical records of a patient in a vehicle control device or a vehicle control method according to an embodiment of the present disclosure.

FIG. 5 shows an example of signaling between a vehicle control device and an external server to obtain medical records of a patient in a vehicle control device or a vehicle control method according to an embodiment of the present disclosure.

Hereinafter, it is assumed that the vehicle control device 101 of FIG. 1 performs the process of FIG. 5, as an example embodiment thereof. Additionally, in the description of FIG. 5, operations described as being performed by the vehicle control device may be understood as being controlled by the processor 107 of the vehicle control device 101, for example.

Referring to FIG. 5, in a first operation 503, a vehicle control device 501 may obtain identification information necessary or useful to identify a patient. According to an embodiment, the identification information may include the patient's name, resident registration number, medical number, or any combination thereof, for example.

In a second operation 505, the vehicle control device 501 may transmit the identification information to an external server or medical facility 521. The external server or medical facility 521 may receive the identification information from the vehicle control device 501.

The vehicle control device 501 may transmit the patient's identification information through wireless communication using a communication protocol for transmitting or receiving medical information (e.g., health level seven (HL7), fast healthcare interoperability resources (FHIR)). This can be to prevent medical information from being leaked.

In a third operation 507, the external server or medical facility 521 may obtain the patient's medical records based on the identification information. The external server or medical facility 521 may identify the patient's stored medical records by retrieving the identification information.

In a fourth operation 509, the external server or medical facility 521 may transmit the medical records to the vehicle control device 501. The vehicle control device 501 may receive the medical records from the external server or medical facility 521.

The vehicle control device 501 may receive the medical records through wireless communication using a communication protocol for transmitting or receiving medical information (e.g., health level seven (HL7) or fast healthcare interoperability resources (FHIR)). This can be to prevent medical information from being leaked.

In a fifth operation 511, the vehicle control device 501 may output medical records. The vehicle control device 501 may output medical records through an output device provided in the host vehicle or medical equipment.

Figure 6:
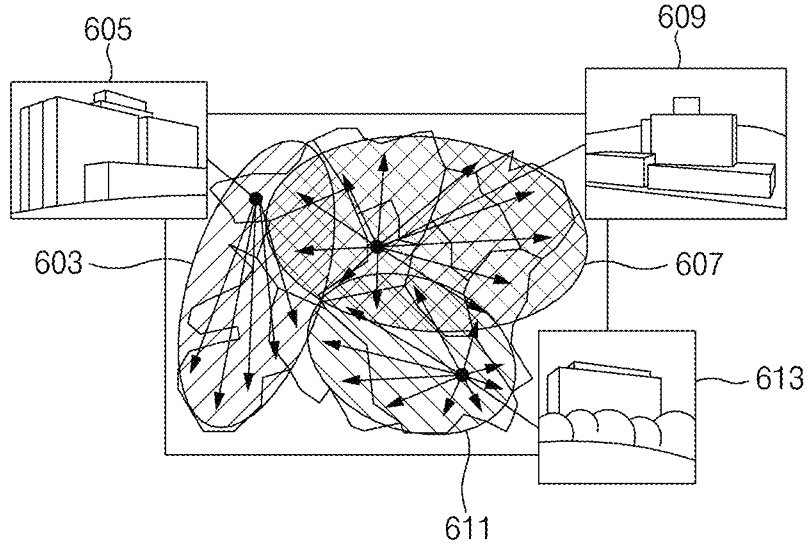
FIG. 6 is a diagram showing an example of a medical service area that is expandable in a vehicle control device or a vehicle control method according to an embodiment of the present disclosure.

FIG. 6 shows an example of a medical service area that can be expandable in a vehicle control device or a vehicle control method according to an embodiment of the present disclosure.

Referring to FIG. 6, a first medical facility 605 may be located in a first area 603. A second medical facility 609 may be located in a second area 607. A third medical facility 613 may be located in a third area 611.

The first medical facility 605 may be a facility that is the focus of medical services in the first area 603. The second medical facility 609 may be a facility that is the focus of medical services in the second area 607. The third medical facility 613 may be a facility that is the focus of medical services in the third area 611.

According to an embodiment, the vehicle control device may drive the host vehicle to a location other than a medical facility and where there is a need to use medical equipment, and provide medical services to a patient at the location other than the medical facility.

For example, patients in a specific area (e.g., the first area 603, the second area 607, or the third area 611) may receive medical services through a vehicle connected by wireless communication to a medical facility associated with a specific area (e.g., the first medical facility 605, the second medical facility 609, and the third medical facility 613).

According to an embodiment, when a specific area (e.g., the first area 603, the second area 607, or the third area 611)

is an area with few medical facilities, medical accessibility for a person living in the specific area may be expanded through the vehicle control device. Additionally, medical accessibility for patients with limited mobility may be expanded.

In a particular example, because renal failure patients need to receive dialysis treatment three times a week for about 5 hours, medical accessibility for renal failure patients in areas with poor medical accessibility may be expanded by the vehicle control device according to an embodiment.

Medical subscription services may be provided to increase medical accessibility for patients living in areas with limited medical facilities or patients with limited mobility. The processor of the vehicle control device may acquire a location included in the medical subscription service and a specified frequency, and perform control such that the host vehicle drives to a location included in the medical subscription service either regularly according to the specified frequency or irregularly upon request. Accordingly, the processor of the vehicle control device may provide medical services to patients through medical equipment either regularly or irregularly upon request or at locations included in the medical subscription service.

Figure 7:
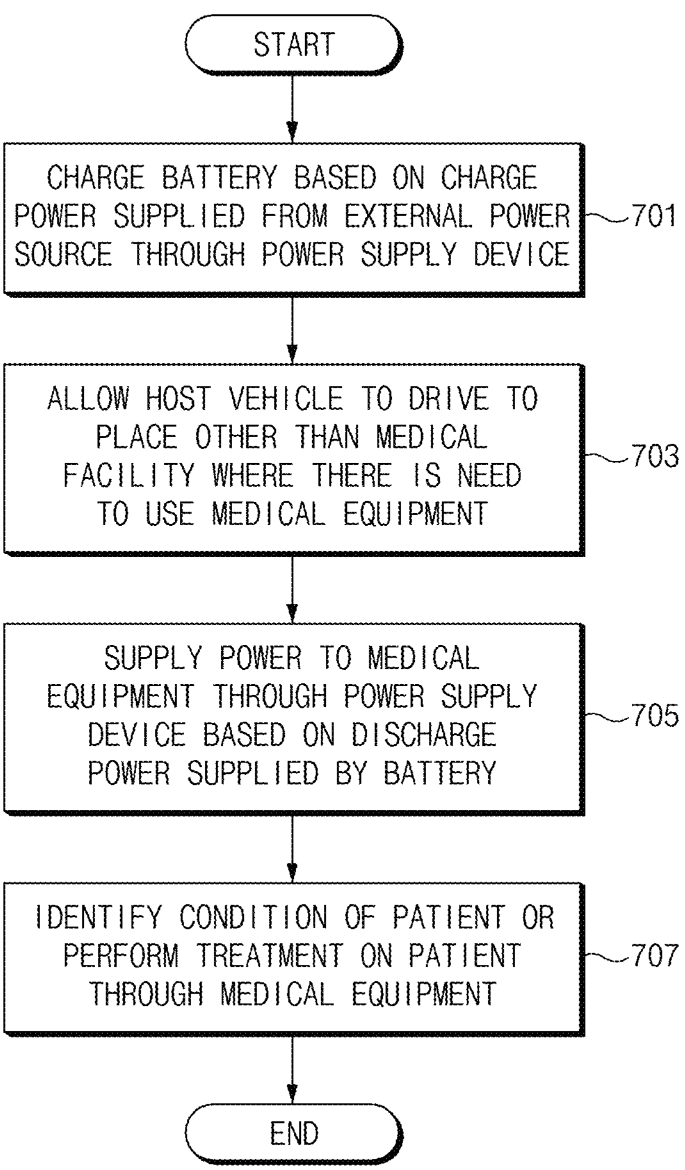
FIG. 7 is a flowchart of operation of a vehicle control device for providing power to medical equipment in a vehicle control device or a vehicle control method according to an embodiment of the present disclosure.

FIG. 7 shows a flowchart of operation of a vehicle control device for providing power to medical equipment in the vehicle control device or a vehicle control method according to an embodiment of the present disclosure.

Hereinafter, it is assumed that the vehicle control device 101 of FIG. 1 performs the process of FIG. 7, as an example embodiment thereof. Additionally, in the description of FIG. 7, operations described as being performed by the vehicle control device may be understood as being controlled by the processor 107 of the vehicle control device 101, for example.

Referring to FIG. 7, in a first operation 701, the processor of a vehicle control device may charge a battery based on a charge power supplied from an external power source through a power supply device. The power supply device may perform charging or discharging and may be included in an electric vehicle which is a host vehicle. The battery may be used to operate the host vehicle.

In a second operation 703, the processor of the vehicle control device may perform control such that the host vehicle drives to a location, other than a medical facility, where there is a need to use medical equipment.

In a third operation 705, the processor of the vehicle control device may provide power to the medical equipment through the power supply device, based on a discharge power supplied by the battery.

In a fourth operation 707, the processor of the vehicle control device may identify a patient's condition and/or perform treatment on the patient through the medical equipment. In other words, the processor of the vehicle control device may provide medical services in locations, other than medical facilities, where there is a need to use medical equipment.

Figure 8:
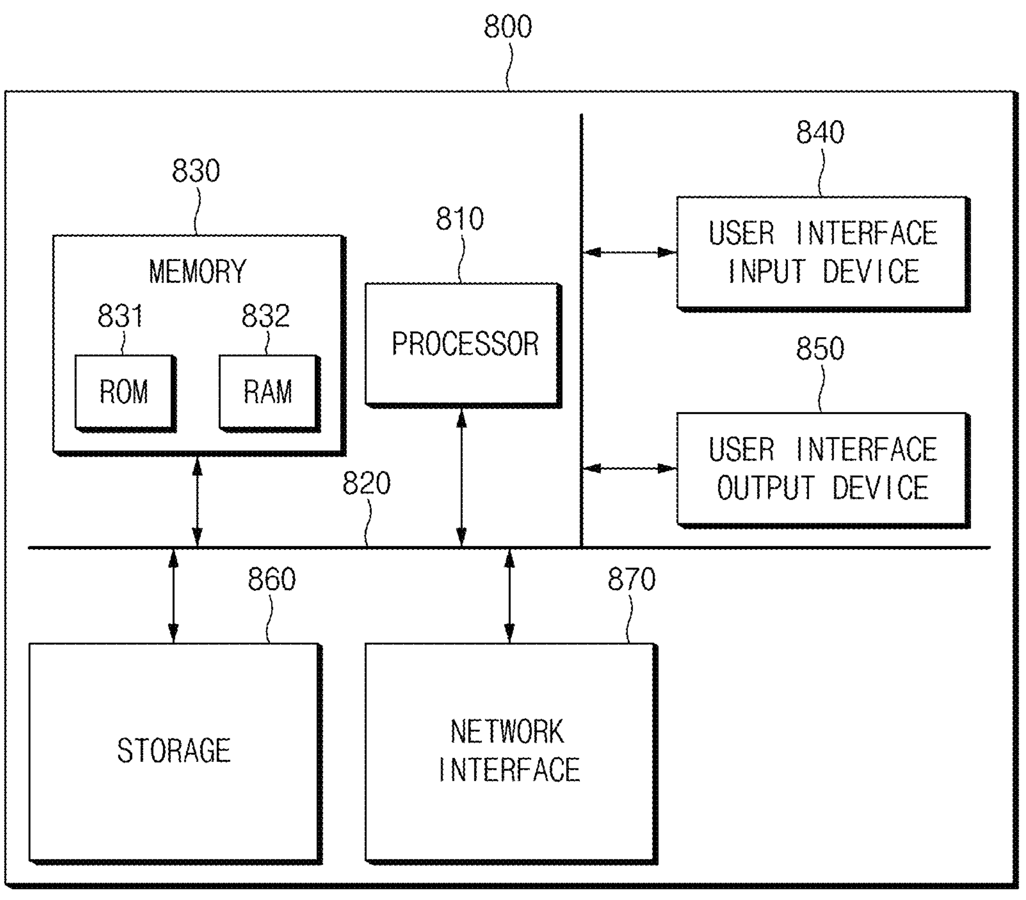
FIG. 8 is a diagram showing a computing system related to a vehicle control device or a vehicle control method according to an embodiment of the present disclosure.

FIG. 8 shows a computing system related to a vehicle control device or a vehicle control method according to an embodiment of the present disclosure.

Referring to FIG. 8, a computing system 800 may include at least one processor 810, a memory 830, a user interface input device 840, a user interface output device 850, storage 860, and a network interface 870, which can be connected with each other via a bus 820, and in which any combination of or all of which may be in plural or may include plural components thereof.

The processor 810 may be a central processing unit (CPU) or a semiconductor device that processes instructions stored in the memory 830 and/or the storage 860. The memory 830 and the storage 860 may include various types of volatile or non-volatile storage media. For example, the memory 830 may include a ROM (Read Only Memory) 831 and a RAM (Random Access Memory) 832.

Thus, the operations of the method or the algorithm described in connection with the embodiments disclosed herein may be embodied directly in hardware or a software module executed by the processor 810, or in a combination thereof. The software module may reside on a storage medium (that is, the memory 830 and/or the storage 860) such as a RAM, a flash memory, a ROM, an EPROM, an EEPROM, a register, a hard disk, a removable disk, and a CD-ROM.

The example storage medium may be coupled to the processor 810, and the processor 810 may read information out of the storage medium and may record information in the storage medium. Alternatively, the storage medium may be integrated with the processor 810. The processor and the storage medium may reside in an application specific integrated circuit (ASIC). The ASIC may reside within a user terminal. In another case, the processor and the storage medium may reside in the user terminal as separate components.

The above description is merely illustrative of technical ideas of the present disclosure, and various modifications and variations may be made without departing from the essential characteristics of the present disclosure by those skilled in the art to which the present disclosure pertains.

Accordingly, the embodiments disclosed in the present disclosure are not intended to limit the technical ideas of the present disclosure but to describe some embodiments of the present disclosure, and the scope of the technical ideas of the present disclosure is not limited by the example embodiments herein. The scope of protection of the present disclosure can be interpreted according to the following claims, and technical ideas within scopes equivalent thereto can be construed as also being included in the scope of the present disclosure.

Some embodiments of the present disclosure may operate medical equipment by providing power from a hybrid vehicle or electric vehicle.

Some embodiments of the present disclosure may improve user convenience by operating medical equipment using power provided from a hybrid vehicle or electric vehicle.

Some embodiments of the present disclosure may expand the scope of medical services available to patients by operating medical equipment using power provided from a hybrid vehicle or electric vehicle.

Some embodiments of the present disclosure may provide medical services to patients who are far away from medical staff by operating medical equipment using power provided by a hybrid vehicle or electric vehicle.

Some embodiments of the present disclosure may operate medical equipment using power provided from a hybrid vehicle or electric vehicle, allowing medical staff in the hybrid or electric vehicle to access the patient's medical records.

Hereinabove, although the present disclosure has been described with reference to example embodiments and the accompanying drawings, the present disclosure is not necessarily limited thereto, but may be variously modified and altered by those skilled in the art to which the present disclosure pertains without departing from the spirit and scope of the present disclosure claimed in the following claims.

What is claimed is:

1. A vehicle control device comprising:

a power supply device included in a host vehicle, the power supply device being configured to perform charging or discharging, wherein the host vehicle is an electric vehicle (EV);

a first battery configured to operate the host vehicle;

a processor; and memory storing instructions that, when executed by the processor, cause the processor to:

charge the first battery based on a charge power supplied from an external power source through the power supply device, perform control of the host vehicle such that the host vehicle drives to a place other than a medical facility for use of medical equipment included in the host vehicle;

provide power to the medical equipment based on a discharge power supplied by the first battery through the power supply device; and control the medical equipment such that the medical equipment performs one of or both of identifying a condition of a patient at the place and performing a treatment on the patient using the medical equipment, wherein the power is supplied to enable use of the medical equipment.

2. The vehicle control device of claim 1, further comprising a communication circuit, wherein the instructions further cause the processor to:

transmit patient condition information obtained through the medical equipment to an external server or a hospital through the communication circuit, receive an opinion of a medical staff according to the patient condition information through the communication circuit; and output the opinion of the medical staff through an output device provided in the host vehicle or the medical equipment.

3. The vehicle control device of claim 2, further comprising a camera and a monitor, wherein the instructions further cause the processor to:

obtain the patient condition information through at least one of the camera or the medical equipment; and output the opinion of the medical staff through the monitor.

4. The vehicle control device of claim 1, further comprising a communication circuit, wherein the instructions further cause the processor to:

transmit identification information for identifying the patient to an external server or a hospital through the communication circuit;

receive a medical record of the patient identified based on the identification information from the external server or the hospital through the communication circuit; and output the medical record through an output device provided in the host vehicle or the medical equipment.

5. The vehicle control device of claim 2, wherein the instructions further cause the processor to:

transmit the patient condition information through wireless communication using a communication protocol for transmitting or receiving medical information; and receive the opinion of the medical staff through the wireless communication using the communication protocol.

6. The vehicle control device of claim 1, wherein the instructions further cause the processor to provide a rated voltage of the medical equipment to the medical equipment through the power supply device, and wherein the power supply device includes an integrated charging control unit (ICCU).

7. The vehicle control device of claim 1, wherein the medical equipment is configured to include at least one of an oxygen supply device, a defibrillator, a dialysis machine, a vital monitor, an aspirator, a laryngoscope, or any combination thereof.

8. The vehicle control device of claim 1, wherein the instructions further cause the processor to provide an interface for operating a vehicle seat such that a seat angle between a lower end of the vehicle seat and a backrest of the vehicle seat is adjusted to a first angle or greater than the first angle.

9. The vehicle control device of claim 1, wherein the instructions further cause the processor to provide an interface for operating a turning seat such that the turning seat is adjusted to face a second seat by rotating the turning seat.

10. The vehicle control device of claim 1, further comprising a spare battery that is different from the first battery, wherein the instructions further cause the processor to continuously supply power to the medical equipment through the spare battery in response to the first battery being discharged after powering the medical equipment with the first battery.

11. The vehicle control device of claim 1, wherein the instructions further cause the processor to:

obtain the place and a specified frequency included in a subscription service;

perform control such that the host vehicle drives to the place regularly according to the specified frequency or irregularly upon request; and perform one of or both of identifying the condition of the patient at the place and performing treatment on the patient through the medical equipment at the place.

12. The vehicle control device of claim 7, wherein the medical equipment includes the dialysis machine, wherein the instructions further cause the processor to supply power to the dialysis machine from the first battery through the power supply device, and wherein the dialysis machine is configured to provide hemodialysis to the patient.

13. A vehicle control method comprising:

charging a first battery of a host vehicle based on a charge power supplied from an external power source through a power supply device of the host vehicle;

performing control such that the host vehicle drives to a place other than a medical facility to use medical equipment included in the host vehicle;

providing power to the medical equipment based on a discharge power supplied by the first battery through the power supply device; and identifying a condition of a patient or performing a treatment on the patient using the medical equipment at the place, wherein identifying or performing using the medical equipment comprises providing the power to the medical equipment based on the discharge power supplied by the first battery through the power supply device.

14. The method of claim 13, further comprising:

transmitting patient condition information obtained through the medical equipment to an external server or a hospital;

receiving an opinion of a medical staff according to the patient condition information; and outputting the opinion of the medical staff through an output device provided in the host vehicle or the medical equipment.

15. The method of claim 14, wherein identifying the condition of the patient comprises obtaining the patient condition information through at least one of a camera or the medical equipment, and wherein the outputting of the opinion of the medical staff through the output device comprises outputting the opinion of the medical staff through a monitor.

16. The method of claim 13, further comprising:

transmitting identification information to identify the patient to an external server or a hospital;

receiving a medical record of the patient identified based on the identification information from the external server or the hospital; and outputting the medical record through an output device provided in the host vehicle or the medical equipment.

17. The method of claim 14, wherein transmitting the patient condition information comprises transmitting the patient condition information through wireless communication using a communication protocol for transmitting or receiving medical information, and wherein the receiving of the opinion of the medical staff comprises receiving the opinion of the medical staff through the wireless communication using the communication protocol.

18. The method of claim 13, wherein providing the power to the medical equipment comprises providing a rated voltage of the medical equipment to the medical equipment through the power supply device that includes an integrated charging control unit (ICCU).

19. The method of claim 13, wherein the medical equipment includes at least one of an oxygen supply device, a defibrillator, a dialysis machine, a vital monitor, an aspirator, a laryngoscope.

20. The method of claim 13, further comprising providing an interface for operating a vehicle seat such that a seat angle between a lower end of the vehicle seat and a backrest of the vehicle seat is adjusted to a first angle or more.

* * * * *